(12) United States Patent
Leonard et al.

(10) Patent No.: US 9,974,591 B2
(45) Date of Patent: May 22, 2018

(54) SYSTEM FOR ATTACHING A PIECE OF OSTEOSYNTHESIS EQUIPMENT

(71) Applicant: TEKNIMED, Vic en Bigorre (FR)

(72) Inventors: Alain Leonard, Nosy BE (MG); Carole Leonard, Paulhac (FR); Cyril Sender, Toulouse (FR); Gautier Halbin, Fontenilles (FR); Olivier Lignon, Ambres (FR); Nouredine Sahraoui, Toulouse (FR)

(73) Assignee: TEKNIMED, Vic en Bigorre (FR)

( * ) Notice: Subject to any disclaimer, the term of this patent is extended or adjusted under 35 U.S.C. 154(b) by 456 days.

(21) Appl. No.: 14/436,896

(22) PCT Filed: Oct. 17, 2013

(86) PCT No.: PCT/FR2013/052478
§ 371 (c)(1),
(2) Date: Apr. 19, 2015

(87) PCT Pub. No.: WO2014/060702
PCT Pub. Date: Apr. 24, 2014

(65) Prior Publication Data
US 2015/0272648 A1    Oct. 1, 2015

(30) Foreign Application Priority Data
Oct. 19, 2012    (FR) .................................... 12 59982

(51) Int. Cl.
*A61B 17/88* (2006.01)
*A61B 90/00* (2016.01)

(52) U.S. Cl.
CPC ...... *A61B 17/8875* (2013.01); *A61B 17/8891* (2013.01); *A61B 90/03* (2016.02); *A61B 2090/036* (2016.02); *F04C 2270/0421* (2013.01)

(58) Field of Classification Search
CPC ..................... A61B 17/8875; A61B 17/8891
See application file for complete search history.

(56) References Cited

U.S. PATENT DOCUMENTS 1,793,259 A * 2/1931 Smeuninx ................ B23G 1/46
279/81
2,361,683 A * 10/1944 Greenberg .......... B23B 31/1075
279/144

(Continued)

FOREIGN PATENT DOCUMENTS

FR            2932078 A1     12/2009

*Primary Examiner* — Zade Coley
(74) *Attorney, Agent, or Firm* — Im IP Law; C. Andrew Im

(57) ABSTRACT

A system for attaching a piece of osteosynthesis equipment against a bone tissue includes at least a screw, and a screwdriver having a handle extended by a rod with an adapter to engage the screw. A portion of the guide member of the screwdriver protrudes in front of the end-piece of the screwdriver and extends along or around a portion of the screw to guide the screw in axial translation. The guide member has a front end forming an abutment of the screwdriver against the surface of the piece of osteosynthesis equipment on completion of a predefined depth of screwing of the screw into the bone tissue. The guide member can be set at a chosen length of extension, corresponding to a predefined depth of insertion of the screw. After insertion, the screw can be severed, and optionally fused with the piece of equipment to reinforce the locking of same.

15 Claims, 2 Drawing Sheets

(56) References Cited

U.S. PATENT DOCUMENTS

| | | | | |
|---|---|---|---|---|
| 2,940,488 A * | 6/1960 | Riley, Jr. | | B25B 23/0064 144/92 |
| 3,336,611 A * | 8/1967 | Schepp | | B25B 21/007 408/202 |
| 3,682,177 A * | 8/1972 | Ames | | A61B 17/1695 403/13 |
| 3,965,510 A * | 6/1976 | Ernst | | B25B 21/007 7/158 |
| 4,521,145 A * | 6/1985 | Bieler | | B23B 49/005 408/202 |
| 4,954,025 A * | 9/1990 | Crawford | | B25B 21/007 408/238 |
| 5,313,680 A * | 5/1994 | Ringler | | B25F 3/00 7/138 |
| 5,524,512 A * | 6/1996 | Wolfe | | B25B 23/0064 81/429 |
| 5,564,717 A * | 10/1996 | Alberts | | B23B 31/00 279/145 |
| 5,586,847 A * | 12/1996 | Mattern, Jr. | | B23B 51/108 279/145 |
| 5,918,685 A * | 7/1999 | Ulbrich | | B23B 49/006 173/15 |
| 6,030,162 A * | 2/2000 | Huebner | | A61B 17/1682 411/263 |
| 6,099,529 A * | 8/2000 | Gertzman | | A61B 17/8605 606/309 |
| 6,162,225 A * | 12/2000 | Gertzman | | A61B 17/861 606/309 |
| 6,506,192 B1 * | 1/2003 | Gertzman | | A61B 17/8605 606/308 |
| 8,057,136 B2 * | 11/2011 | Chiang | | B23B 45/003 279/14 |
| 2005/0010226 A1 * | 1/2005 | Grady, Jr. | | A61B 17/746 606/281 |
| 2006/0079903 A1 * | 4/2006 | Wong | | A61B 17/1735 606/916 |
| 2007/0005077 A1 * | 1/2007 | Null | | A61B 17/862 606/104 |
| 2008/0097458 A1 * | 4/2008 | Donahoe | | A61B 17/862 606/104 |
| 2010/0274298 A1 | 10/2010 | Schiff | | |

* cited by examiner

SYSTEM FOR ATTACHING A PIECE OF OSTEOSYNTHESIS EQUIPMENT

RELATED APPLICATIONS

This application is a § 371 application from PCT/FR2013/052478 filed Oct. 17, 2013, which claims priority from French Patent Application No. 12 59982 filed Oct. 19, 2012, each of which is herein incorporated by reference in its entirety.

TECHNICAL FIELD OF THE INVENTION

The present invention belongs to the field of surgical instruments and more particularly concerns fixation systems used in bone repair. It relates to a system for fixation of an osteosynthesis instrument against a bone tissue, this system comprising at least a fastening screw and associated equipment comprising a screwdriver.

BACKGROUND OF THE INVENTION

Osteosynthesis comprises all methods which make it possible to hold two bone structures in place following a fracture, an arthrodesis or an osteotomy. It is used, for example, when the reduction (that is to say realignment of the bone ends) cannot be done by external manipulation or when the two fragments are not stable. It uses various instruments for holding together the two fragments of the bone (or a bone and an implant), such as plates, rods, nails, screws, pins, staples, etc. The aim is to achieve consolidation of the bone in the anatomical position.

Osteosynthesis with the aid of an instrument such as a plate screwed by means of one or more screws has been used in bone surgery for decades. Holding of the bone is then ensured by the plate, which is fixed to the bone fragments to be joined with the aid of a plurality of screws passing through said instrument and the bone tissue. The screws used for holding the instrument may be of different diameters and different lengths, depending on the shape of the instrument and the position of the implantation.

These screws conventionally comprise a relief in the upper part of the head, which will cooperate with a screwdriver whose tip is of complementary shape: screw with a slotted or cross head, or a hollow head (for example cooperating with a male screwdriver with 6 contact surfaces). They are made available to the surgeon at the time of the intervention at the same time as specific equipment dedicated to positioning the fixation system, generally comprising drills, a screw tap and a screwdriver.

Osteosynthesis using an instrument such as a plate associated with one or more screws is regarded as a reliable means for obtaining good bone consolidation, when it can be carried out properly. To this end, a certain number of conditions need to be satisfied, or at least sought, among which the quality of the screwing has a very important role. It is essential for the instrument to be tightly secured to the bone as soon as it is implanted and over the course of time. It is therefore imperative for the screws to remain in place despite the vibrations and other stresses which may create a play and lead to their loosening. The screws therefore need to be securely anchored both to the bone and to the instrument.

It is also necessary to be able to orientate the screw at a suitable angle, which the surgeon will select according to the bone parameters of the patient. The screws may thus be inserted along an axis perpendicular to the instrument, but it is often necessary to impart a certain inclination to them with respect to a right angle, particularly in order to reach a bone fragment far from the fracture region. For this reason, the head of the screw cannot be fully engaged in the cavity (recess) provided for this purpose in the instrument and projects on the surface.

The devices formed by an osteosynthesis instrument such as a plate, and screws, provided to surgeons have for a long time been made of metal, generally titanium or stainless steel. Currently, the best metal devices are locked and orientable devices. Each cavity intended to receive a screw head then consists of a lug having a certain degree of mobility relative to the instrument. The locking is carried out using a second screw thread formed on the lower part of the head of the screw, the first screw thread corresponding to the shaft of the screw engaging with the bone. This second screw thread is received in a complementary screw thread formed at the lug. When the lug is mounted in an orientable fashion, this locking device may furthermore be inclined in a suitable direction, commonly in a radius of the order of 0 to 15° in all directions.

The metals or metal alloys used, although tolerated well by the body, have two drawbacks. On the one hand, since the instrument, often in the form of a plate, is only rarely removed (in about 15% of cases), it must participate in the long term in the kinematic function of the organ which it has made it possible to resolve. However, its presence has the effect that the mechanical stresses are not transmitted homogeneously into the bone in question. This results in weakening of the bone at the points of contact between the bone and the instrument, namely essentially at the screws. Secondary fractures are therefore frequent.

In order to overcome this problem, osteosynthesis devices comprising an instrument, for example in the form of a plate, and one or more screws made of polymers have been proposed. Biocompatible polymers such as PEEK (polyether ether ketone), implantable polyamides, UHMWPE (ultra-high molecular weight polyethylene) or PETs (polyethylene terephthalates), may be used. They offer the advantage of less rigidity, which reduces the mechanical stresses imposed on the bone. More recently, an alternative has been proposed which is based on the use of resorbable polymers, which have the advantage of progressively disappearing in the body, but at the end of a time delay sufficient for the bone to have recovered its solidity. For example, polymers belonging to the family of PLAs (polylactic acids), PCLs (polycaprolactones), PDSs (polydioxanones) and PGAs (polyglycolic acids), as well as copolymers thereof, are known.

Whether or not they are resorbable, all these polymers have a major drawback: they are radiotransparent. For this reason, it is not possible to monitor their position during their implantation or subsequently with radiographic techniques. A new generation of osteosynthesis devices has recently been developed by the Applicant, which are produced with the aid of a composite mixture of materials that progressively degrade, comprising a polymer or copolymer compound and an inorganic filler provided by a ceramic.

There are therefore now a range of nonmetallic osteosynthesis implants offering new advantages to the surgeon. However, a certain number of drawbacks remain to be overcome.

It has been seen that, in metal osteosynthesis devices, the connection between the instrument and the or each screw is reinforced by locking. However, devices produced on the basis of polymers (including a composite mixture of polymer and ceramic) cannot use this type of fixation. This is because the techniques for shaping polymer materials do not make it possible to produce a thin screw thread on the surface, which in any event would not withstand the mechanical stresses (essentially friction) during screwing. The polymer screws known to date comprise a conical or hemispherical head and are placed perpendicular to the overall plane of the instrument, often a plate, or with a maximum angle of 5° with respect to this plane. It is not possible to lock them like metal screws. This constitutes a significant drawback of polymers compared with metal.

In order to solve this problem, a system for holding polymer-based osteosynthesis instruments has been developed, using headless screws, also polymer-based, these being fitted with the aid of a screwdriver designed and dedicated specifically to these screws.

It has been found that it is possible to carry out locking of the screws on synthetic polymer materials by welding the surfaces in contact. Specifically, the nature of the materials used can be exploited in order, on the one hand, to cut the screw after insertion to a desired depth in the bone in order to remove the protruding rear part after insertion, and on the other hand to weld the screw and the associated instrument together by surface fusion of the materials, induced by an electric knife. The shaft of the screw is thus melted in the surface in the lug of the instrument through which it passes.

This being the case, the rear part of the screw is eliminated, making sure that the screw does not protrude from the surface of the bone. The screw can then be inserted into the instrument in any direction with a high inclination (which may be up to 30°), without creating a perturbing projection, while an osteosynthesis device with metal screws allows maximum inclinations of only 15°. Thus, unexpectedly, a lockable and orientable device is obtained which performs better than the metal screw/instrument device.

However, such a device raises a new problem, which is the basis of the present invention. It is in fact indispensable to monitor the insertion depth of the screws into the bone tissue. This is particularly important because, in numerous indications, it is recommended for the screws to pass fully through the bone in order to grip the external walls of the cortical bone at two opposite points. The cortical bone refers to the external wall of the bones, which imparts rigidity and elasticity to them. It is formed of a dense layer of calcified tissue, which surrounds the medullary cavity filled with bone marrow. One difficulty for the surgeon then resides in fine assessment of the insertion length which is sufficient for the bicortical fixation, but without the screw, referred to as a bicortical screw, protruding excessively from the surface of the bone.

Conventionally, during an operation, the surgeon will determine the necessary screw length, in particular by means of a depth gauge, then select screws of suitable length from a range of screws available to him, and fit them by screwing thoroughly until the screwing end of the screw, most often its head, is blocked in contact with the plate. Such a method of fixing the screws involves the use of screws provided with a head, while such a procedure cannot be adopted in the case of a screw intended to be cut.

OBJECT AND SUMMARY OF THE INVENTION

The problem on which the present invention is based is therefore, for a system for fixation of an osteosynthesis instrument against a bone tissue, this system being composed of at least one screw and a screwdriver, to monitor precisely the insertion depth of the screw into the bone tissue and into the osteosynthesis instrument applied against said tissue.

To this end, the present invention provides a system for fixation of an osteosynthesis instrument against a bone tissue, this system comprising at least i) a screw having a threaded shaft and a rear end, and ii) a screwdriver having a handle extended by a rod, the end of which carries an adapter suitable for cooperating with the rear end of the screw, in which system the screw consists of a material comprising a polymer and said screwdriver is equipped with a guide member connected to the rod for guiding the screw, with one portion of the guide member projecting in front of the adapter of the screwdriver such that it extends along or around a part of the screw in order to guide it in axial translation, said guide member having a front end forming a stop of the screwdriver against the surface of the osteosynthesis instrument when a predefined screwing depth of the screw in the bone tissue is reached.

In the description which follows, unless otherwise indicated, the fixation system to which the invention relates will be presented in a configuration in which the screw is in place on the screwdriver, and in an orientation in which its front part points toward the instrument to be fixed, while its rear part is the one which faces toward the operator. The various members constituting it will also be oriented according to this convention.

The screwdriver makes it possible to carry out the screwing of a screw to a selected and predefined depth, generally measured with the aid of a depth gauge. In what follows, the screwing depth will correspond to the depth of the hole made in the bone plus the thickness of the osteosynthesis instrument through which the screw passes. This screwing depth is selected and predefined, generally by the surgeon: it corresponds to the degree of penetration of the screw in order to ensure robust fixation.

Of course, the screwing depth of the screw refers to the length of screw which has progressed into the bone (plus the thickness of the instrument), the corollary of which is that the progression of the front end of the screw is monitored to a level which is desired for the fixation, and which may be different from one occasion to another. In the system according to the invention, it is not the length of the screw which is selected as a function of the degree of insertion to be reached. Neither is it the position of the rear end of the screw (arriving flush with the osteosynthesis instrument to be fixed) which causes the end of the advance of the screw, as is the case in other known systems such as the one described for example in FR 2 932 078. Rather, according to the invention the length of the screw is universal, it is inserted as far as desired, and after fitting of the screw the protruding rear part of the screw is removed by cutting it.

The screw is cut easily since it consists of a material comprising a polymer, on its own or as a mixture with another material, the hardness of which is much less than that of conventional screws made of metal or metal alloys.

The system according to the invention can be used with types of assemblies other than the fixation of an osteosynthesis instrument against a bone tissue. The screw is inserted into the guide member until its rear end comes into contact with the adapter of the screwdriver. The adapter will then be capable of cooperating with the rear end of the screw in order to impart a rotational movement to it when the user manipulates the screwdriver.

One portion of the guide member projects in front of the adapter of the screwdriver, so that said portion extends in front of the adapter along or around a part of the screw, in order to guide it in axial translation during the screwing phase. Guiding in axial translation is carried out by an annular linear connection which opposes transverse translations (radial with respect to the axis of the rod). All the other movements are free. This guiding is expediently ensured by the front end of the guide member, with the aid of an annular linear link having sufficient play to allow the translational movement to take place freely, without resistance. The practitioner can exert a force on the system without fearing deviation of the tool or undesirable flexion of the screw.

The guide member fulfills a second function, since its front end will form a stop of the screwdriver against the surface of the osteosynthesis instrument when the desired screwing depth is reached. Specifically, as is conventional, the screw and the screwdriver cooperate during the screwing but are separated once the screw is fitted. It is commonly the operator who visually assesses that the screw has entirely penetrated into the parts to be fixed, and who, by reducing the pressure which he exerts on the handle of the screwdriver, separates its tip from the head of the screw. In an original way, according to the invention, this separation takes place when, the front end of the guide member having come into contact with the osteosynthesis instrument, the screwdriver can no longer advance. With the operator continuing to impart to the screwdriver its rotational movement, the screw will for its part continue its advance so that its rear end will progressively be disengaged from the adapter of the screwdriver. The screw is fully released and its advance is stopped as soon as its tip has reached the depth initially selected. Even if the operator persists, the screw will not advance further.

Thus, according to the present invention, the guide member which forms a stop against the wall of the osteosynthesis instrument is an element independent of the screw. It fulfills two functions, ensuring on the one hand guidance of the screw during the screwing, and on the other hand ending of the screwing at a predefined depth by disconnecting the screw and the screwdriver. In this way, a screw can be fitted with a precise and selected insertion depth, the depth being determined beforehand by means available to the practitioner (for example with the aid of a depth gauge).

Once the screwing depth has been determined, according to the invention the position of the stop can be modified as a function of said depth. It is possible to provide a plurality of positions of the guide member on the rod, corresponding to different insertion depths of the screw. According to a preferred characteristic of the invention, the guide member is mounted so as to slide on the rod, means being provided for locking said member in at least one position in the length of the rod. This position corresponds to the predefined screwing depth of the screw, and it dictates the portion of said member which it is necessary to make extend in front of the adapter. A stop is thus produced which can be adjusted by sliding the guide member on the rod in order to obtain a selected extension length.

Advantageously, said guide member is in the form of a tube, the front end of which is provided with an orifice allowing axial translation of the screw. The tube is mounted on the rod, which it partially encloses and on which it can slide. Its front end, which fulfills the function of a stop, is pierced with an orifice allowing the screw to pass through. It can be tightened with respect to the body of the tube so as to leave only the play necessary for the screw to advance, while holding it effectively in the screwing axis.

Preferably, the locking means are in the form of a knurled wheel having an axle which passes through the guide member and is blocked on the rod. A knurled wheel is a means of releasable securing of the guide member on the rod, which is suitable for adjustment of the length of the guide member extending beyond the adapter of the screwdriver, while being easily manipulable by the practitioner by simple rotation.

Although it can be used with any type of screw, the screwdriver according to the invention is entirely suitable for fitting a headless screw. This is why, advantageously, the screw used in the system according to the invention is a headless screw, the rear end of the screw not projecting laterally from the shaft of the screw (beyond the edge of the screw thread). The cross section of such a screw therefore has a diameter identical or at least similar to that of the shaft over its entire length.

This characteristic is advantageous in several regards. On the one hand, the orifice of the guide member can have a diameter scarcely greater than that of the screw, so as to ensure its guidance effectively. On the other hand, the absence of a projection on the screw allows it to pass fully through the orifice of the guide member. Not only is it possible to put the screw in position on the screwdriver through the orifice of the guide member without having to separate the latter, but above all the screwdriver and its guide member can be removed after the screwing has been carried out. Lastly, particularly beneficially, the screw can be screwed with a large inclination with respect to the normal without being hampered by having to fit a screw head in the lug of the osteosynthesis material to be fixed, since the bulk at the lug due to a projecting head is eliminated. It is possible to reduce the size of the holes provided on the osteosynthesis instrument, which increases its rigidity compared with an instrument having chamfered holes for a headed screw.

According to a preferred characteristic of the invention, the screw is made of optionally resorbable polymer material, or of a composite mixture of at least a polymer and a ceramic. The screw used in the fixation system may consist 100% of a thermoplastic polymer such as PEEK, PEKK, implantable polyamides, UHMWPEs, PETs, or of PLA, the latter being bioresorbable. It is also possible to use a screw made of a composite material combining a resorbable polymer and a resorbable ceramic. The ceramic may, for example, be selected from calcium sulfates, calcium phosphates, calcium carbonate, silicates, in particular bioglasses, and will preferably be calcium-strontium hydroxyapatite or tricalcium phosphate. The advantage of this composition resides, on the one hand, in its breakdown rate which is faster than that of an osteosynthesis instrument made of polymer alone, and on the other hand in the fact that it is radiopaque.

These plastic and/or composite materials have the advantage of being easy to cut. The surgeon can cut the rear part of the screw protruding from the implantation site with the aid of simple pliers, for example, and will not have to select a screw of precise length before operating. When the desired length of screw has penetrated into the bone, it will be possible to cut the excess rear part of the screw flush with the osteosynthesis instrument, then fuse it with the instrument at the lug in order to reinforce its locking with the osteosynthesis instrument. Surgeons will thus be provided with screws with the various working diameters but only one length. This limits the number of references with which the surgeon is provided.

Particularly advantageous cooperation can therefore be obtained between the headless screws made of polymer or composite and the screwdriver of the fixation system. It will however be noted that, since the polymer or composite materials are not as strong as the metals normally used, it is preferable for the rear end of the screw and the adapter of the screwdriver to be well adapted to the stresses which they will experience, particularly during the screwing. This is why it is proposed for the screw to comprise a rear part, in extension of the threaded shaft, allowing secure albeit temporary connection of the screw and the screwdriver. Thus, according to a particular embodiment of the invention, the screw has an unthreaded axial extension continuing the threaded shaft and ending at the rear end, said rear end and the adapter having complementary engageable male and female shapes. This makes it possible to provide the screw with a screw thread only over a portion for which this screw thread is necessary.

This also makes it possible to give the rear part of the screw a smaller thickness than the adapter of the screwdriver, so that the latter can grip the rear of the screw in order to hold it correctly, even if the polymer material has a tendency to deform. This is why, preferably, the rear end of the screw constitutes the male shape and the adapter constitutes the female shape.

Also preferably, the rear extension of the screw has the shape of a spatula, that is to say a blade which is wider than it is thick. In this case, the adapter of the screwdriver is preferably a U-shaped mandrel suitable for receiving the end of the rear extension of the screw. The use of a mandrel is particularly suitable for securing, to the rear extension of the screw, which is releasable but remains firm during the rotation of the screwdriver, in order to contribute to holding of the screw when it experiences torsion. At the end of screwing, when the front end of the guide member arrives at the stop, the spatula will disengage spontaneously and easily from the U-shaped limbs of the mandrel, until fully separating therefrom, thus freeing all of the screwdriver. It will then be sufficient to remove the guide member from the rear part of the screw still protruding, cut the latter flush with the plate and optionally fuse it with the plate by means of an electric knife.

Preferably, in the case in which the adapter of the screwdriver is a U-shaped mandrel, this adapter is provided with a removable sleeve for reinforcing the strength of the mandrel during the screwing.

The adapter of the screwdriver may have various shapes, so long as the rear end of the screw is shaped complementarily. It may furthermore be interchangeable, which makes it possible to keep the same screwdriver body for screwing screws of different types by changing only the screwing adapter. This also makes it possible to use the same screwdriver body while associating other tools with it for work other than screwing, for example drilling and/or tapping the instrument and the bone tissue.

It is convenient to be able to read the insertion depth of the screw, predefined as explained above, directly on an element of the screwdriver visible to the practitioner. This is because, the exact position of the guide member with respect to the rod corresponding to the desired insertion depth of the screw, it is advantageous to have precise references in order to make the guide member slide along the rod as far as the desired length. This is why, advantageously, the rod of the screwdriver comprises means for visualizing the adjustment of the position of the guide member with respect to the rod.

In order to do this, it is for example possible to make the guide member of transparent material, so that the rod remains visible, the latter bearing references along its length. It is also possible to provide a window formed in the guide member. According to a preferred embodiment, the display means comprise a graduated scale carried by the rod and a slot formed in the guide member, making it possible to see at least a part of said scale. The scale may comprise graduations in the same unit as used on the depth gauge. Once the appropriate extension of the system has been achieved, the guide member is fixed on the rod with the aid of the locking means adopted, for example a knurled wheel.

It will be noted that it is expedient to take into account the way in which the adapter and the rear of the screw are connected, particularly in the case in which the adapter has the shape of a mandrel, this having a certain depth. Specifically, when the guide member has reached the stop, the screw is still connected to the mandrel. It will advance a little further, so that its rear end will progressively disengage from the grip of the mandrel, in order finally to be released therefrom. The depth of the mandrel should therefore be taken into account in the graduation of the scale, by offsetting the origin enough for the screw to reach the previously measured depth before separation of the adapter and the screw.

The screwdriver of the system according to the invention comprises a handle for the operator to hold it in his hand. The handle of the screwdriver may comprise a holding member mounted freely in rotation. The practitioner can thus continue to rotate the tool without releasing its pressure on the handle.

By virtue of the fixation system comprising screws and a suitable screwdriver, it is now possible to fit screws, advantageously made of polymer, in a way which is convenient, secure and reliable over the course of time. This allows the use of osteosynthesis instruments made of polymer materials while no longer entailing the difficulties which have hitherto limited their widespread use in surgery. The system is therefore better performing than a metal screw/osteosynthesis instrument assembly the maximum orientations of which are limited.

BRIEF DESCRIPTION OF THE DRAWINGS

The present invention will be understood more clearly, and details relevant thereto will become apparent, from the description which will be given of one of its alternative embodiments, in connection with the appended figures in which.

DETAILED DESCRIPTION OF THE EMBODIMENTS

Figure 1A:
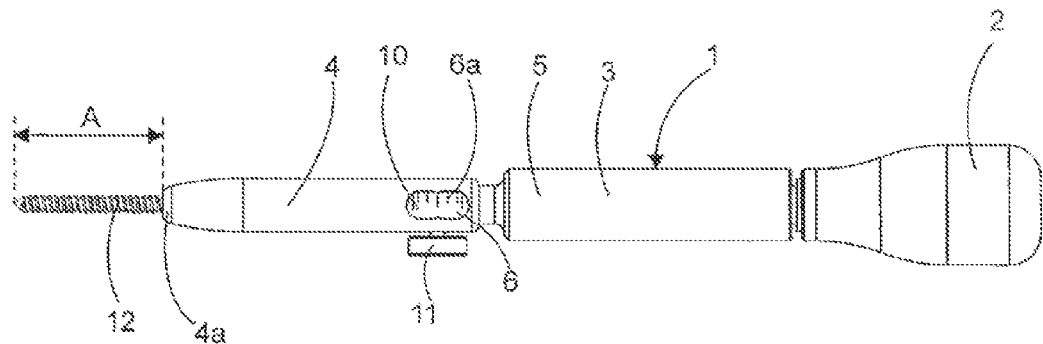
FIG. 1 represents a single screwdriver and a screw forming part of the fixation system according to the invention. It is detailed in FIGS. 1a, 1b and 1c, in which the guide member is engaged on the rod to a greater or lesser extent.
Figure 1B:
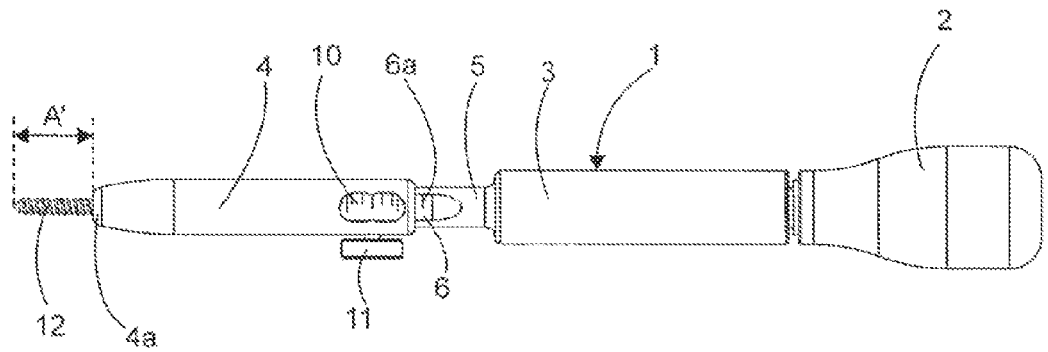
Figure 1C:
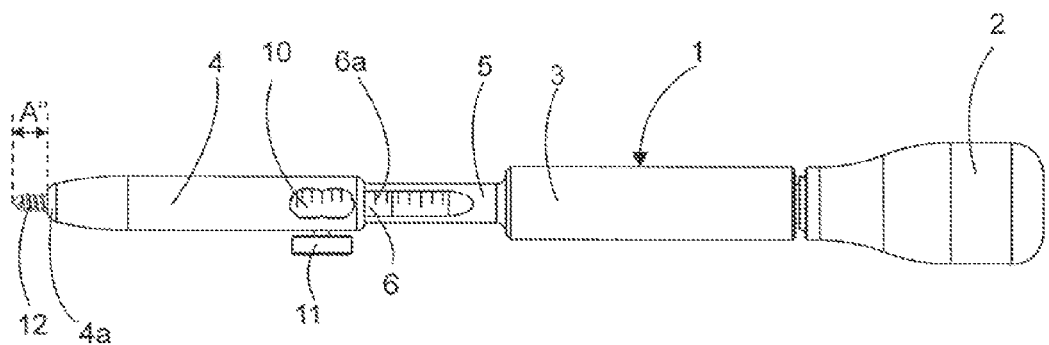
Figure 2:
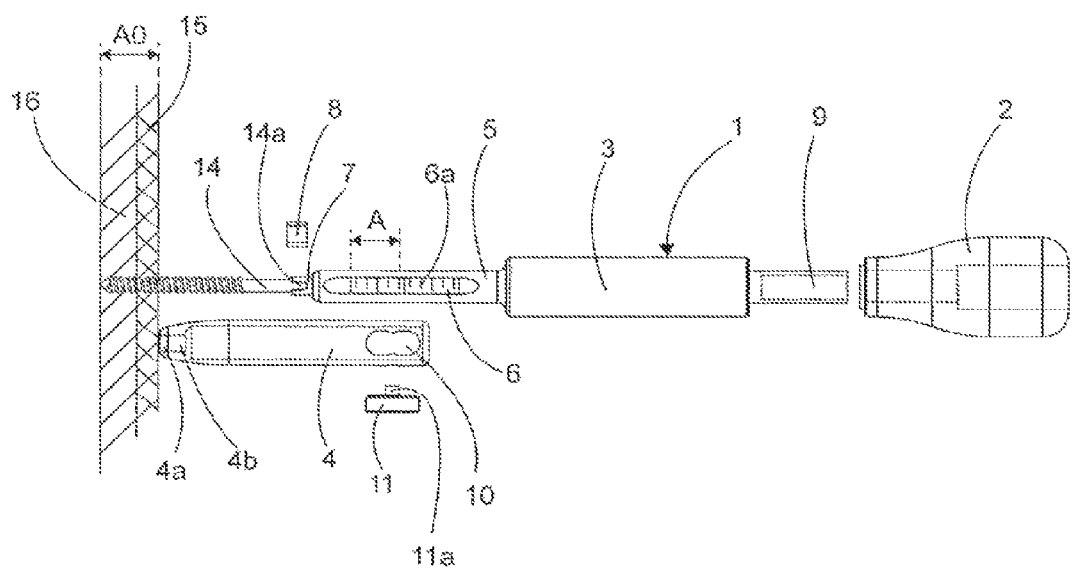
FIG. 2 represents an exploded view of the system according to the invention, the parts being arranged at the distance which they occupy in relation to the site of insertion of the screw.

FIGS. 1 and 2 represent a screwdriver 1 and a screw 12 intended to be screwed into a bone tissue 16 receiving an osteosynthesis instrument, in this case a plate 15. The screwdriver 1 and the screw 12 form part of the system for fixation of an osteosynthesis instrument according to the present invention. The screw 12 has a threaded shaft 13 intended to be inserted by screwing through the osteosynthesis plate 15 and the bone tissue 16. The threaded shaft is continued by the rear extension 14 carrying the rear end 14a.

The screwdriver 1 comprises a cylindrical handle 3 extending in the length of the screwdriver 1. The handle 3 is provided with a holding element 2, which may have various shapes, for example a knob or a T. The handle 3 comprises an axle 9 extending it at its end facing toward the holding element 2 and used for engagement of the latter. It is possible to motorize the screwdriver 1 by adding to it motorized means secured to the axle 9.

The handle 3 is extended by the cylindrical rod 5, the front end of which is mounted on the adapter 7 forming the front of the screwdriver 1. In what follows, for the elements of the screwdriver 1, the term front will refer to any element facing toward the screw 12.

During its use, the rod 5 of the screwdriver 1 is partially covered by the member 4, which will be described in detail below, for guiding the screw 12. This guide member 4 has a portion which extends forward beyond the adapter 7.

The rod 5 comprises, on part of its external surface, display means consisting of a slot 10 revealing the scale 6 bearing graduations, in order for the surgeon, the user of the screwdriver 1, to adjust the extension length forward of the portion of the guide member 4 extending beyond the screwdriver 1, this being in order to obtain a desired insertion depth for the screw 12.

The front end of the screwdriver 1 carries the adapter 7, which cooperates with the rear end 14a of the screw 12. In some embodiments, the adapter 7 may be removable so that the screwdriver 1 can be provided with different screwing shapes cooperating with different complementary shapes provided on the rear end 14a of the screwdriver 12.

The adapter 7 has a central recess receiving the rear end 14a, this recess allowing the screw 12 to be temporarily secured to the screwdriver 1 during screwing. In FIG. 2, the adapter 7 is in the form of a U-shaped mandrel receiving the rear end 14a and making it possible to hold it when the screw 12 experiences torsion. The adapter 7 is covered with the protective sleeve 8, which surrounds it while allowing the rear end of the screw 12 to pass into the adapter 7. The sleeve 8 may be removable or, conversely, mounted in a fixed fashion, for example by welding.

The guide member 4 has the shape of a hollow tube which partially covers a part of the rod 5 of the screwdriver 1 while enclosing it, and it extends in front of the screwdriver 1 so that it can receive a part of the screw 12 inside it. At its front end 4a, the guide member 4 is provided with an orifice 4b sufficient to allow the screw 12 to advance. It is thus used for guiding the screw 12 in axial translation, the screw 12 penetrating therein through its front opening 4a when the screwdriver 1 is placed in the screwing position. The guide member 4 is also used as a stop for the screwdriver 1, with its front end 4a abutting against the wall of the osteosynthesis plate 15 when a predefined insertion depth of the screw 12 into the bone tissue 16 has been reached. Said insertion depth cannot be exceeded since the screw 12 and the screwdriver 1 are decoupled because of the guide member 4 abutting against the plate 15.

Figure 3:
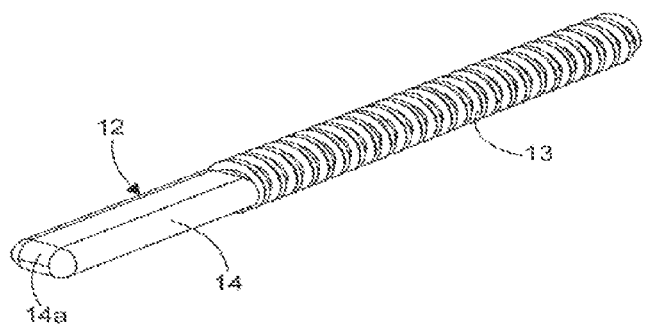
FIG. 3 is a perspective view of a screw forming part of the fixation system according to the present invention.

As shown in FIGS. 1 to 3, the guide member 4 is advantageously in the form of a tube covering a part of the screw 12 and of the rod 5. It can slide along the rod 5 of the screwdriver 1. It comprises a knurled wheel 11 having an axle 11a fixed radially by screwing against the rod 5 of the screwdriver 1, while passing through the wall of the guide member 4. The guide member can thus be locked in a selected position. The slot 10 formed on the guide member 4 allows the practitioner to see the graduations 6a of the scale 6 during the positioning and subsequent locking of the guide member 4 on the rod 5.

The fixation system according to the invention may comprise a plurality of types of screws of different sizes and/or different shapes. The screw presented in the present exemplary embodiment (FIG. 3) of the invention is a headless screw. The screw 12 comprises the threaded shaft 13 continued by an unthreaded axial extension 14 carrying the rear end 14a not projecting laterally from the shaft of the screw 12. The threaded shaft 13 has a circular cross section, the rear extension 14 for its part having a substantially rectangular cross section, which gives it the shape of a spatula. This shape is entirely suitable for cooperating with the adapter 7 having the form of a U-shaped mandrel.

It is also possible to provide a circular rear extension 14 or a circular threaded shaft 13 without an axial extension. In both cases, the rear end 14a of the screw 12 may have at least one part in axial projection or at least one reception recess cooperating respectively with a reception recess or a part in axial projection provided on the adapter of the screwdriver.

Use of the Fixation System

FIGS. 1a, 1b and 1c show the same screwdriver, but with a different adjustment. An identical screw in all three cases has been fitted on the screwdriver, by inserting it through the orifice 4b into the guide member 4 until its rear end 14a has entered the adapter 7. As can be seen, the length of the screw (denoted A, A' and A") extending beyond the front end 4a of the guide member 4 is related to the degree of retraction of the guide member 4 on the rod 5.

The extension length of the guide member 4 in front of the screwdriver 1 can thus be fixed precisely. In practice, the depth of the hole intended to receive the screw 12 is read with the aid of a tool such as a depth gauge, and, according to this insertion depth predefined in this way of the screw, the guide member 4 is slid to the corresponding position on the rod 5, found by direct reading on the scale, and locked. The desired insertion depth of the screw 12 into the plate 15 and the tissue 16 is thus subtracted from the length of the screw 12 by adjusting the positioning of the guide member 4.

It is furthermore necessary to take into account the way in which the adapter and the rear of the screw are connected, particularly in the case in which the adapter has the shape of a mandrel, this having a certain depth. Once the guide member has arrived at the stop, the screw will continue to advance a small distance so that the rear end of the screw will progressively disengage from the grip of the mandrel, in order finally to be completely released therefrom. The depth of the mandrel should therefore be taken into account in the graduation of the scale, by offsetting the origin sufficiently.

In FIG. 2, the exploded representation of the system according to the example shows the correspondence between the penetration depth Ao of the screw through the plate 15 and into the bone 16 and the position of the slider 6a on the scale 6 at the retraction distance A of the guide member. During screwing into the bone tissue 16, the screw 12 will be inserted through the plate 15 then the bone tissue 16, so that the front end 4a of the guide member 4 will approach the wall of the plate 15. When the screw 12 has penetrated to the depth Ao (less the penetration depth of the rear of the screw into the mandrel), the front end 4a of the guide member 4 comes to abut against the plate 15. Further rotation of the screwdriver 1 will cause the screw to advance, while the screwdriver is now blocked, causing progressive withdrawal then separation of the rear end 14a of the screw from the adapter 7. Fine calibration makes it possible to take account of the fact that the material of the screw will deform under the torsion force experienced, and the depth of the limbs of the mandrel. The scale 10 is therefore calibrated to correspond exactly to the predetermined depth Ao.

In order to obtain effective bicortical fixation, as illustrated in FIG. 2, the screw 12 passes fully through the thickness of the plate 15 and of the tissue 16, but it should not protrude too far on the other side of the bone tissue. This is now possible by virtue of the system according to the invention. That which has been described above is valid for all depths of insertion by screwing of the screw 12 into an osteosynthesis plate 15 or other instrument, and bone tissue 16.

The screws 12 may have varied compositions, for example composed 100% of at least one polymer. It is possible to use polylactic acids (or PLAs) so that they have an elasticity allowing them to be wedged in the osteosynthesis plate 15. In general, the screws 12 may be made of optionally resorbable polymer, or a mixture of optionally resorbable polymers, or of a composite mixture of at least one polymer and one or more ceramics.

The system is particularly suitable for the fixation of a plate, or other instrument, made of optionally resorbable polymer, with the aid of screws also composed of such materials, as explained above. Once the screw has been inserted and the screwdriver has been removed, the remaining part is cut flush with the plate, which is readily possible so long as the material forming the screw is of a polymer or polymer-based composite type. The braking force of the screw 12 forcibly held in the plate 15 and the bone tissue 16 is then the same as the breaking force of a screw head. In order to obtain even better locking of the screw 12 in the plate 15, it is possible to hot-weld the screw 12 and the plate 15, for example with the aid of an electric knife.

The invention claimed is:

1. A system for fixation of an osteosynthesis instrument against a bone tissue, comprising at least a screw having a threaded shaft and a rear end; and a screwdriver having a handle extended by a rod, the end of which carries an adapter configured to cooperate with the rear end of the screw; wherein the screw consists of a material comprising a polymer; wherein the screwdriver comprises a guide member connected to the rod to guide the screw, with one portion of the guide member projecting in front of the adapter of the screwdriver and extending along or around a part of the screw to guide the screw in axial translation; wherein the screw is inserted freely in translation into the guide member; wherein said guide member is mounted to slide on the rod and comprises a locking mechanism to lock the guide member in at least one position in a length of the rod corresponding to a predefined screwing depth of the screw, the guide member comprises a front end forming a stop of the screwdriver against the surface of the osteosynthesis instrument when a predefined screwing depth of the screw in the bone tissue is reached, causing the screwdriver to be blocked and the screw to advance to the stop by a separation of the rear end of the screw from the adapter.

2. The system as claimed in claim 1, wherein the guide member is in a form of a tube, the front end of the tube comprises an orifice configured to allow the axial translation of the screw.

3. The system as claimed in claim 1, wherein the locking mechanism is in a form of a knurled wheel comprising an axle which passes through the guide member and is blocked on the rod.

4. The system as claimed in claim 1, wherein the screw is a headless screw, the rear end of the screw not having a lateral projection.

5. The system as claimed in claim 1, wherein the screw is made of polymer material.

6. The system as claimed in claim 5, wherein the polymer material is resorbable.

7. The system as claimed in claim 1, wherein the screw is made of a composite polymer and ceramic mixture.

8. The system as claimed in claim 1, wherein the screw comprises an unthreaded axial extension continuing the threaded shaft and ending at the rear end; and wherein the rear end of the screw and the adapter of the screwdriver have complementary engageable male and female shapes.

9. The system as claimed in claim 8, wherein the rear end of the screw constitutes the male shape and the adapter constitutes the female shape.

10. The system as claimed claim 9, wherein the unthreaded axial extension of the screw has a shape of a spatula.

11. The system as claimed in claim 1, wherein the adapter is a U-shaped mandrel configured to receive the rear end of the unthreaded axial extension of the screw.

12. The system as claimed in claim 11, wherein the adapter comprises a removable reinforcing sleeve.

13. The system as claimed in claim 1, wherein the rod of the screwdriver comprises a display to visualize an adjustment of the position of the guide member with respect to the rod.

14. The system as claimed in claim 1, further comprising a display comprising a graduated scale carried by the rod and a slot formed in the guide member to view at least a part of the scale.

15. The system as claimed in claim 1, wherein the handle of the screwdriver comprises a holding member mounted freely in rotation.

* * * * *